United States Patent
Wheaton et al.

(10) Patent No.: US 10,719,934 B2
(45) Date of Patent: Jul. 21, 2020

(54) DEVICES, SYSTEMS, AND METHODS FOR MEDICAL IMAGING

(71) Applicant: CANON MEDICAL SYSTEMS CORPORATION, Otawara-shi (JP)

(72) Inventors: Andrew J. Wheaton, Shaker Heights, OH (US); Antonios Matakos, Solon, OH (US)

(73) Assignee: CANON MEDICAL SYSTEMS CORPORATION, Otawara-shi (JP)

(*) Notice: Subject to any disclaimer, the term of this patent is extended or adjusted under 35 U.S.C. 154(b) by 100 days.

(21) Appl. No.: 16/163,449

(22) Filed: Oct. 17, 2018

(65) Prior Publication Data

US 2020/0126213 A1 Apr. 23, 2020

(51) Int. Cl.
| | |
|---|---|
| *G06T 7/00* | (2017.01) |
| *A61B 5/055* | (2006.01) |
| *A61B 6/03* | (2006.01) |
| *A61B 8/08* | (2006.01) |
| *G06T 11/00* | (2006.01) |
| *G06T 15/08* | (2011.01) |
| *A61B 5/00* | (2006.01) |

(52) U.S. Cl.
CPC .............. *G06T 7/0012* (2013.01); *A61B 5/055* (2013.01); *A61B 6/032* (2013.01); *A61B 6/037* (2013.01); *A61B 5/0064* (2013.01); *A61B 8/483* (2013.01); *G06T 11/005* (2013.01); *G06T 15/08* (2013.01); *G06T 2207/10081* (2013.01); *G06T 2207/10104* (2013.01); *G06T 2207/30004* (2013.01)

(58) Field of Classification Search
CPC ......... G06T 2207/10072; G06T 11/008; G06T 2207/10081; G06T 2207/10088; G06T 7/0012
See application file for complete search history.

(56) References Cited

U.S. PATENT DOCUMENTS

| | | | | |
|---|---|---|---|---|
| 6,792,071 | B2* | 9/2004 | Dewaele | G06T 7/0012 378/51 |
| 6,904,163 | B1* | 6/2005 | Fujimura | G06T 7/0012 378/162 |
| 8,120,683 | B1* | 2/2012 | Tumer | H01L 27/14634 250/370.09 |
| 8,214,020 | B2* | 7/2012 | Aulbach | A61B 5/416 600/425 |

(Continued)

OTHER PUBLICATIONS

Roohi, S., et al., "Super-Resolution MRI Images Using Compressive Sensing", 20th Iranian Conference on Electrical Engineering, (ICEE2012), May 15-17, 2012, pp. 1618-1622.

*Primary Examiner* — Yosef Kassa
(74) *Attorney, Agent, or Firm* — Oblon, McClelland, Maier & Neustadt, L.L.P.

(57) ABSTRACT

Devices, systems, and methods for generating a medical image receive scan data, wherein the scan data is defined in an acquisition space; perform a first reconstruction process to generate a lower-resolution image based on the scan data, wherein the first reconstruction process uses a subset of the scan data; and perform a second reconstruction process to generate a higher-resolution image based on the scan data, wherein the second reconstruction process uses more of the scan data than the subset of the scan data.

24 Claims, 7 Drawing Sheets

(56) References Cited

U.S. PATENT DOCUMENTS

| | | | |
|---|---|---|---|
| 8,463,360 B2 * | 6/2013 | Yamamoto | A61B 90/36 |
| | | | 600/407 |
| 8,594,399 B2 * | 11/2013 | Bernhardt | G06T 19/00 |
| | | | 382/128 |
| 8,699,773 B2 | 4/2014 | Akcakaya et al. | |
| 8,867,807 B1 * | 10/2014 | Fram | G06F 19/321 |
| | | | 382/128 |
| 2014/0296702 A1 | 10/2014 | Griswold et al. | |
| 2015/0346305 A1 | 12/2015 | King | |

* cited by examiner

DEVICES, SYSTEMS, AND METHODS FOR MEDICAL IMAGING

BACKGROUND

Technical Field

This application generally concerns medical imaging.

Background

Medical imaging produces images of the internal members of a patient's body. For example, magnetic resonance imaging (MRI) uses radio waves, magnetic fields, and magnetic-field gradients to produce images of the internal members of a patient's body. Medical-imaging modalities also include, for example, X-ray radiography, ultrasonography, computed tomography (CT), and positron emission tomography (PET). Once the images have been produced, a physician can use the images to diagnose a patient's injuries or diseases.

Also, some medical-imaging devices use compressed sensing. Compressed sensing reconstructs images using a lower sampling rate than the rate required by the Nyquist-Shannon sampling theorem. Compressed sensing takes advantage of an image's sparsity within a given domain. Some examples of a domain in which an image may be sparse include the spatial domain (conventional three-dimensional space), time domain (for a time series of images), or wavelet domain (data produced via wavelet transform). Compressed sensing is able to recover the image using the lower sampling rate using iterative reconstruction methods, which are typically slow and computationally expensive.

SUMMARY

Some embodiments of a method comprise receiving scan data, wherein the scan data is defined in an acquisition space; performing a first reconstruction process to generate a lower-resolution image based on the scan data, wherein the first reconstruction process uses a subset of the scan data; and performing a second reconstruction process to generate a higher-resolution image based on the scan data, wherein the second reconstruction process uses more of the scan data than the subset of the scan data.

DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Figure 1:
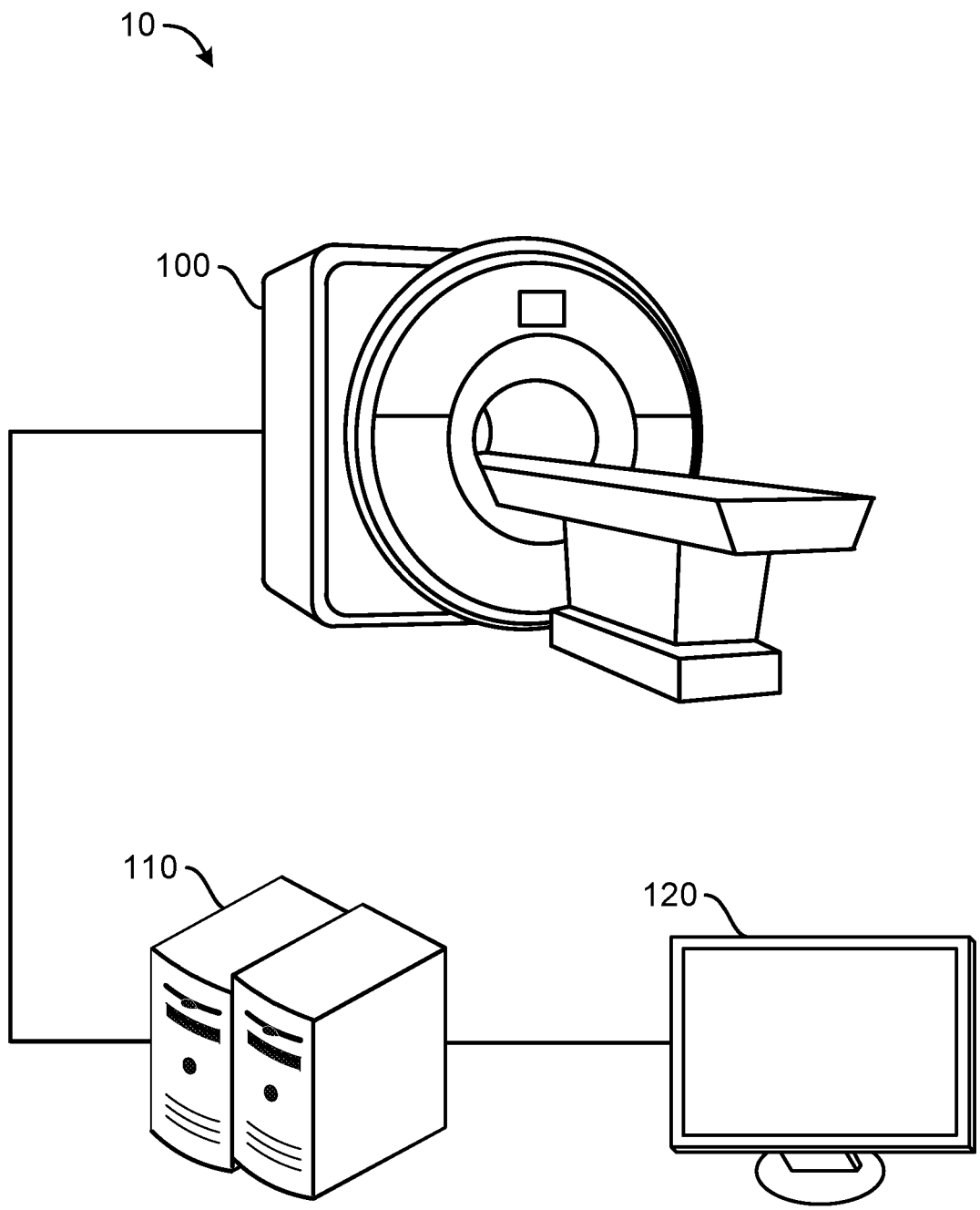
FIG. 1 illustrates an example embodiment of a medical-imaging system.

FIG. 1 illustrates an example embodiment of a medical-imaging system 10. The medical-imaging system 10 includes at least one scanning device 100; one or more image-generation devices 110, each of which is a specially-configured computing device (e.g., a specially-configured desktop computer, a specially-configured laptop computer, a specially-configured server); and a display device 120.

The scanning device 100 is configured to acquire scan data by scanning a region (e.g., area, volume, slice) of an object (e.g., a patient). The scanning modality may be, for example, magnetic resonance imaging (MRI), computed tomography (CT), positron emission tomography (PET), X-ray radiography, and ultrasonography. The scanning device 100 may acquire a randomly undersampled set of scan data that is appropriate for compressed-sensing reconstruction or acquire scan data that may be used by a compressed-sensing process. Accordingly, compressed-sensing data includes scan data that may be used by a compressed-sensing process or that is appropriate for compressed-sensing reconstruction.

The one or more image-generation devices 110 obtain scan data from the scanning device 100 and generate an image of the region of the object based on the scan data. To generate the image, for example when the scan data is compressed-sensing data, the one or more image-generation devices 100 may perform a reconstruction process on the scan data. Examples of reconstruction processes include GRAPPA, SENSE, ARC, SPIRiT, LORAKS, ISTA, and FISTA. If the scan data is compressed-sensing data, then the reconstruction process may be a non-linear process that enforces both the sparsity of the image representation within a given domain (e.g., spatial, time, wavelet) and the consistency of the reconstruction with the acquired scan data.

After the one or more image-generation devices 110 generate the image, the one or more image-generation devices 110 send the image to the display device 120, which displays the image.

Also, the one or more image-generation devices 110 may generate two images from the same scan data. The one or more image-generation devices 110 may use different reconstruction processes to generate the two images from the same scan data, and one image may have a lower resolution than the other image. Additionally, the one or more image-generation devices 110 may generate an image by using only a subset of the scan data, and this image may also have a lower resolution. The one or more image-generation devices 110 can send the lower-resolution image to the display device 120, which then displays the lower-resolution image, while the one or more image-generation devices 110 are still generating the higher-resolution image.

In some embodiments, the lower-resolution image is sent to a display device 120 that is used by the operator of the scanning device 100 or that is adjacent to the scanning device 100, and the higher-resolution image is sent to a physician's display device. The operator of the scanning device 100 often wants to quickly observe images to confirm that the images capture the desired information, and the operator may want to plan the next scan(s) of the scanning device 100 using the images from the previous scan(s). Furthermore, if the operator must wait for one or a few minutes before viewing a previous scan's images, the workflow is interrupted.

Thus, the lower-resolution image may be particularly advantageous to the operator of the scanning device 100. Although a physician typically wants to use an image that has the highest-possible resolution to perform a diagnosis, the operator of the scanning device 100, who may have a patient on site, may not need an image that has the highest-possible resolution to determine if the scan successfully captured the desired data. Moreover, the one or more image-generation devices 110 may need several minutes to generate the higher-resolution image. The one or more image-generation devices 110 can generate the lower-resolution image faster than they can generate the higher-resolution image, and the lower-resolution image may be adequate for the operator's purposes. For example, rather than wait for the higher-resolution image, the operator can use the lower-resolution image to confirm that a scan captured the desired data, to plan the next scan (e.g., the field of view (FOV) of the next scan), and to confirm that the patient's motion was within acceptable parameters while a scan was performed. Accordingly, using the lower-resolution image may decrease or eliminate some delays in the operator's workflow and allow the operator to scan more patients.

Figure 2:
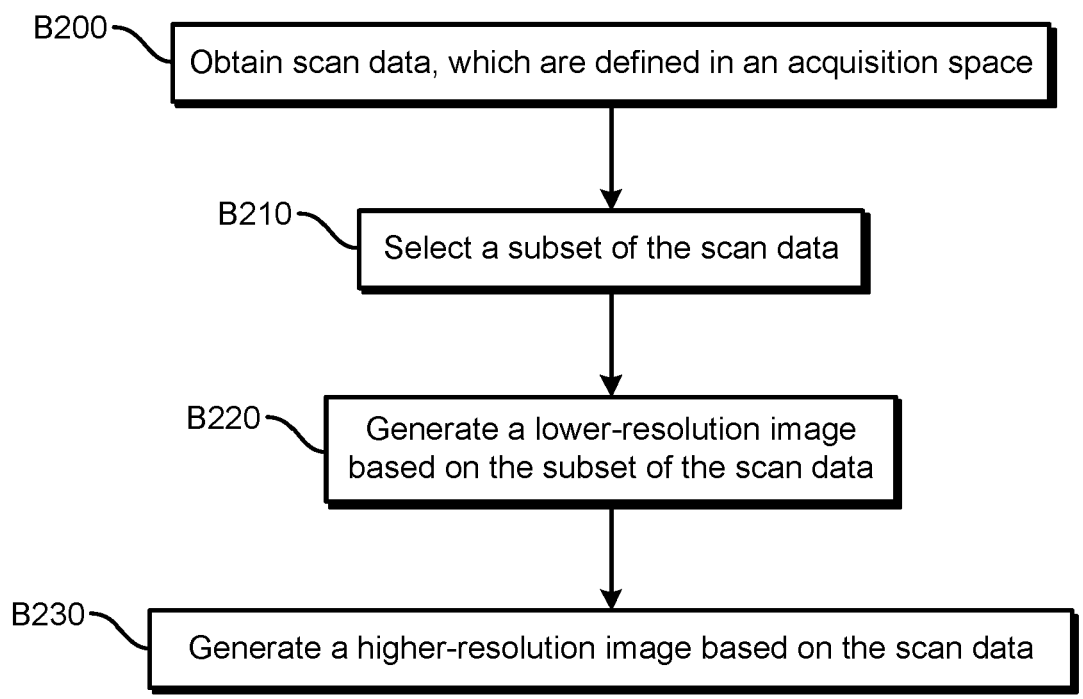
FIG. 2 illustrates an example embodiment of an operational flow for generating images from scan data.

FIG. 2 illustrates an example embodiment of an operational flow for generating images from scan data. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. Thus, other embodiments of the operational flows that are described herein may omit blocks, add blocks, change the order of the blocks, combine blocks, or divide blocks into more blocks.

Furthermore, although this operational flow and the other operational flows that are described herein are performed by an image-generation device, some embodiments of these operational flows are performed by two or more image-generation devices or by one or more other specially-configured computing devices.

The operational flow in FIG. 2 starts in block B200, wherein the image-generation device obtains scan data, which are defined in an acquisition space. For example, if the scan modality is MRI, then the acquisition space may be k-space, and the k-space data may be acquired using collection methods such as Cartesian sampling, Spiral sampling, and Radial sampling. If the scan modality is CT, then the acquisition space may be projection space, commonly referred to as a sinogram. Also, the scan data may be compressed-sensing data. Next, in block B210, the image-generation device selects a subset of the scan data.

The flow then moves to block B220, where the image-generation device generates a lower-resolution image, which is defined in an image space, based on the subset of the scan data. The lower-dimensional image may be a two-dimensional image or a three-dimensional image (e.g., an image volume, a stack of two-dimensional images). To generate the lower-resolution image, for example when the subset of scan data includes randomly-undersampled data, the image-generation device may perform a compressed-sensing reconstruction process on the scan data. In the case where the subset of scan data is fully sampled, a simple, linear, non-iterative reconstruction (e.g., Fourier transform) may be performed. If the subset of scan data is regularly under-sampled, a parallel-imaging reconstruction (e.g., SENSE, GRAPPA, ARC) may be performed. In all of these examples, the reconstruction of the subset of scan data is faster than the reconstruction of the full set due to the smaller size of the subset or the simpler, non-iterative reconstruction method employed (e.g., Fourier transform, parallel-imaging reconstruction). Also, the image-generation device may send the lower-resolution image to a display device before starting or finishing block B230.

Finally, in block B230, the image-generation device generates a higher-resolution image, which is defined in the image space, based on the scan data. The higher-dimensional image may be a two-dimensional image or a three-dimensional image. In block 230, the image-generation device uses more of the scan data than it uses in block B220. In some embodiments, the image-generation device uses all of the scan data to generate the higher-resolution image in block B230. Additionally, to generate the higher-resolution image, for example when the scan data includes compressed-sensing data, the image-generation device may perform a reconstruction process on the scan data. Furthermore, in embodiments where the image-generation device uses a reconstruction process in both blocks B220 and B230, the image-generation device may use a different reconstruction process in each block.

Figure 3:
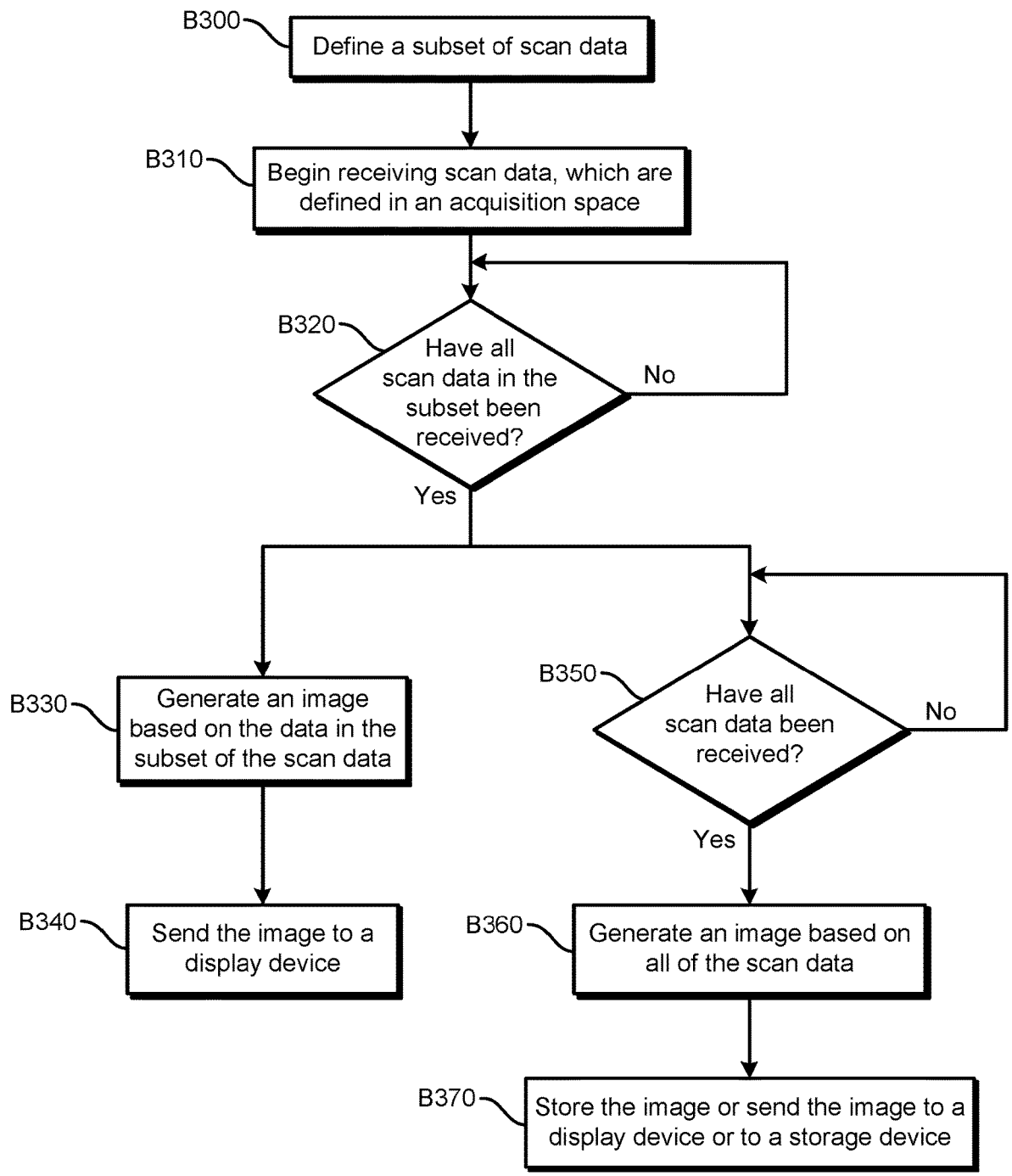
FIG. 3 illustrates an example embodiment of an operational flow for generating an image from scan data and an image from a subset of the scan data.
Figure 4:
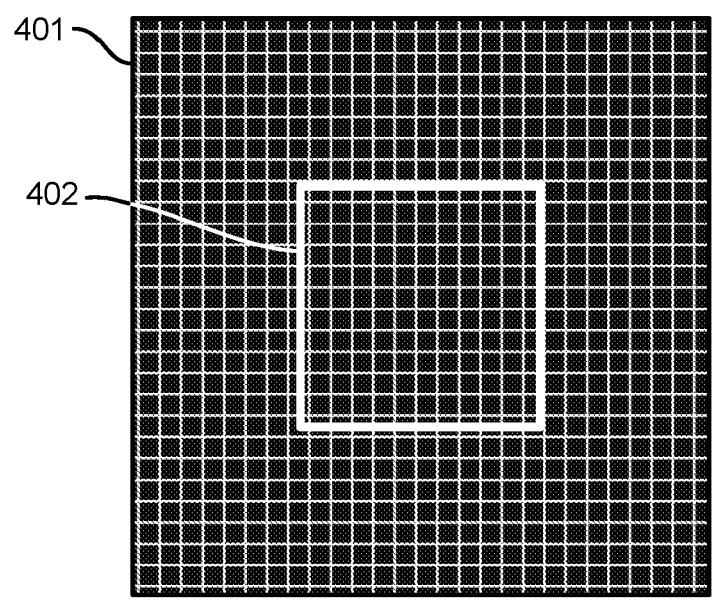
FIG. 4 illustrates an example embodiment of a subset in acquisition space.

FIG. 3 illustrates an example embodiment of an operational flow for generating an image from scan data and an image from a subset of the scan data. The flow starts in block B300, where an image-generation device defines or delimits a subset of scan data, for example by identifying a subset of the acquisition space. FIG. 4 illustrates an example embodiment of a subset 402 of an acquisition space 401. For example, when using MRI scan data, the acquisition space 401 may be k-space, and the image-generation device may define a central area of k-space as the subset 402.

While performing block B300, the image-generation device may obtain one or more user inputs that define or delimit the subset. These inputs may allow a user to adjust the size of the subset. For example, if a user would like an image that has a higher resolution, then, in some embodiments, the user can enter an input to increase the size of the subset. Also for example, if a user wants an image that can be generated faster, then, in some embodiments, the user can enter an input to decrease the size of the subset.

Next, in block B310, the image-generation device begins receiving scan data, for example from a scanning device. The scan data are defined in an acquisition space, and the scan data may be compressed-sensing data. The flow then moves to block B320, where the image-generation device determines if all scan data in the subset of scan data have been received. If not (block B320=No), then the flow returns to block B320. If all scan data in the subset of scan data have been received (block B320=Yes), then the flow splits into a first flow and a second flow. The first flow proceeds to block B330, and the second flow proceeds to block B350. Some embodiments of the image-generation device simultaneously perform the first flow and the second flow.

In block B330, the image-generation device generates an image based on the data in the subset of the scan data. Because the image-generation device uses only the subset of the scan data to generate this image, the image that the image-generation device generates in block B330 may have a lower-resolution than the image that the image-generation device generates in block B360. Also, the image-generation device may be able to perform block B330 faster than block B360. For example, the image-generation device may use the same reconstruction process in blocks B330 and B360, but the image-generation device may be able to perform block B330 faster because block B330 uses only a subset of the scan data. Also for example, in block B330 the image-generation device may use a reconstruction process that is faster than the reconstruction process that the image-generation device uses in block B360.

Furthermore, in some embodiments, the image that the image-generation device generates in block B330 has the same field of view as the image that the image-generation device generates in block B360. For example, if the scan data are defined in a k-space, and the subset of the scan data is an area (e.g., a central area) in the k-space, then the image that is generated in block B330 can have the same field of view as the image generated in block B360, even though the image-generation device uses only a subset of the scan data to generate the image in block B330.

The first flow then moves to block B340, where the image-generation device sends the image that it generated in block B330 to a display device.

The second flow moves from block B320 to block B350. In block B350, the image-generation device determines if it has received all of the scan data. If not (block B350=No), then the second flow returns to block B350. If yes (block B350=Yes), then the second flow proceeds to block B360. In block B360, the image-generation device generates an image based on all of the scan data. In some embodiments, although the image-generation device uses more of the scan data in block B360 than it uses in block B330, the image-generation device does not use all of the scan data in block B360. Finally, the second flow moves to block B370, where the image-generation device stores the image (e.g., on one or more computer-readable storage media) or sends the image to a display device or to a storage device (e.g., an image server).

Also, in some embodiments the image-generation device performs the operations in one or both of blocks B330 and B340 before the image-generation device determines that it has received all scan data in block B350 or before the image-generation device finishes block B360.

Figure 5:
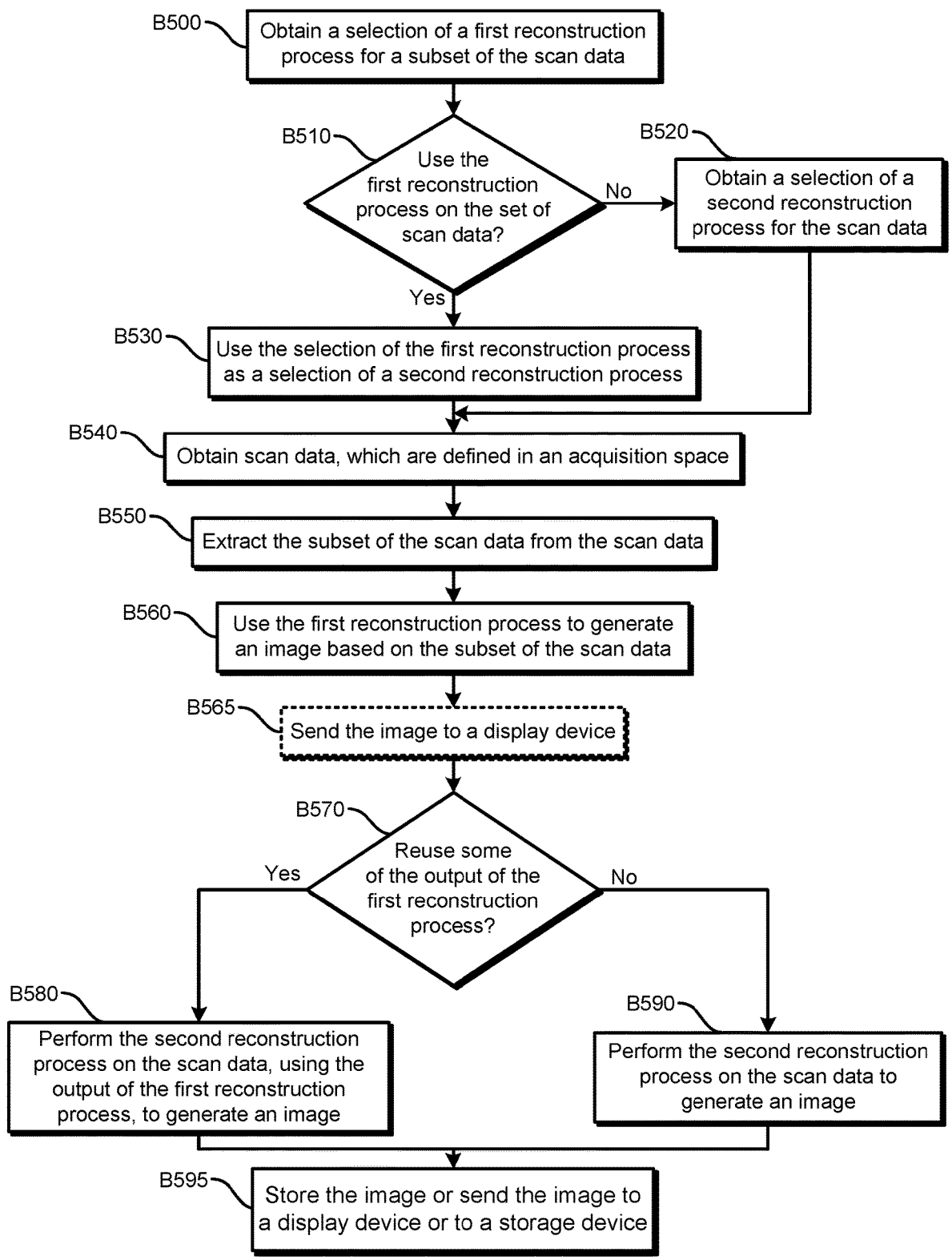
FIG. 5 illustrates an example embodiment of an operational flow for generating images from scan data using at least one reconstruction process.

FIG. 5 illustrates an example embodiment of an operational flow for generating images from scan data using at least one reconstruction process. Some embodiments of the operational flow may implement the following variations: (1) The operational flow may (i) use the same reconstruction process on the subset of the scan data that the operational flow uses on the full set of scan data and (ii) reuse some of the output from the reconstruction of the subset in the reconstruction of the full set. (2) The operational flow may (i) use the same reconstruction process on the subset of the scan data that the operational flow uses on the full set of scan data and (ii) not reuse any of the output from the reconstruction of the subset in the reconstruction of the full set. (3) The operational flow may (i) use a reconstruction process on the subset of the scan data that is different from the reconstruction process that the operational flow uses on the full set of scan data and (ii) reuse some of the output from the reconstruction of the subset in the reconstruction of the full set. (4) The operational flow may (i) use a reconstruction process on the subset of the scan data that is different from the reconstruction process that the operational flow uses on the full set of scan data and (ii) not reuse any of the output from the reconstruction of the subset in the reconstruction of the full set.

The flow starts in block B500, where an image-generation device obtains a selection of a first reconstruction process, which will be performed on a subset of the scan data. For example, the image-generation device may receive the selection of the first reconstruction process from a user.

Next, in block B510, the image-generation device determines whether to use the first reconstruction process on the set of scan data. The image-generation device may make this determination based on a user input. If the image-generation device determines to use the first reconstruction process on the set of scan data (block B510=Yes), then the flow moves to block B530, where the image-generation device uses the selection of the first reconstruction process as a selection of a second reconstruction process. The flow then proceeds to block B540.

If in block B510 the image-generation device determines not to use the first reconstruction process on the set of scan data (block B510=No), then the flow proceeds to block B520. In block B520, the image-generation device obtains (e.g., from a user) a selection of a second reconstruction process to use on the set of scan data, and then the flow moves to block B540. In some embodiments in which the image-generation device performs block B520, the image-generation device can perform the first reconstruction process faster than it can perform the second reconstruction process.

Next, in block B540, the image-generation device obtains scan data, which are defined in an acquisition space. The scan data may include compressed-sensing data. The flow then moves to block B550, where the image-generation device extracts the subset of the scan data from the scan data. Then in block B560, the image-generation device performs the first reconstruction process on the subset of the scan data, thereby generating an image. After block B560, some embodiments of the flow proceed to block B565, in which the image-generation device sends this image to a display device.

Next, in block B570, the image-generation device determines whether to reuse at least some of the output of the first reconstruction process from block B530 when performing the second reconstruction process. If yes (block B570=Yes), then the flow moves to block B580, where the image-generation device performs the second reconstruction process on the scan data, using at least part of the output of the first reconstruction process from block B560, to generate an image. For example, some embodiments of the image-generation device reuse an ESPIRiT map. The operational flow then proceeds to block B595.

If in block B570 the image-generation device determines not to reuse at least some of the output of the first reconstruction process from block B560 (block B570=No), then the flow proceeds to block B590, where the image-generation device performs the second reconstruction process on the scan data to generate an image. The flow then moves to block B595, where the image-generation device stores the image or sends the image to a display device or to a storage device.

Also, in some embodiments, the image-generation device uses more of the scan data in blocks B580 and B590 than it uses in block B560, but does not use all of the scan data in blocks B580 and B590.

Figure 6:
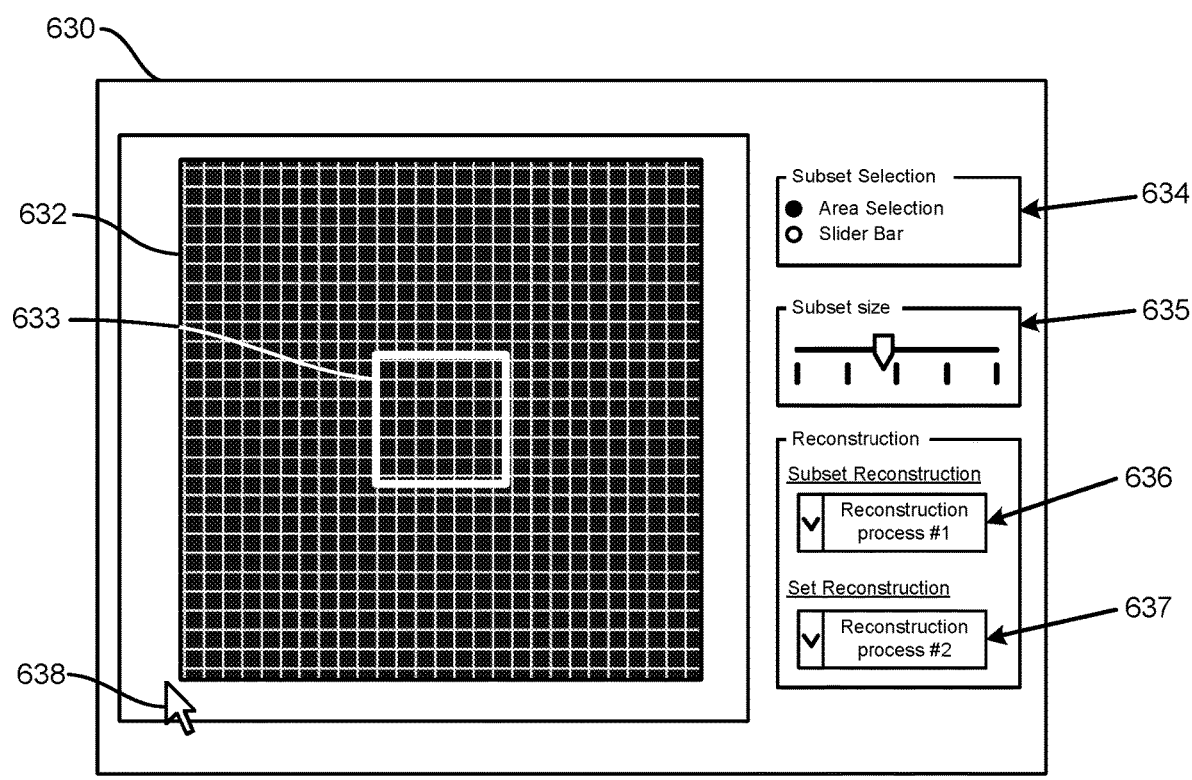
FIG. 6 illustrates an example embodiment of a user interface.

FIG. 6 illustrates an example embodiment of a user interface. The user interface 630, which may be generated by an image-generation device and displayed by a display device, allows a user to select the size of a subset of scan data and select two reconstruction processes for the scan data.

The user interface 630 includes an acquisition-space representation 632 and a subset representation 633. The user interface 630 also includes a subset-selection control 634 that allows the user to choose between selecting the subset by using a cursor 638 to select an area of the acquisition-space representation 632 or by using a slider bar 635. The slider bar 635 allows a user to increase or decrease the size of the subset. The user interface 630 may change the size of the subset representation 633 in accordance with a user's operation of the slider bar 635.

Additionally, the user interface 630 includes two drop-down menus. A subset-reconstruction drop-down menu 636 allows a user to select a reconstruction process for use on a subset of scan data, and a set-reconstruction drop-down menu 637 allows a user to select a reconstruction process for use on the set of scan data.

Figure 7:
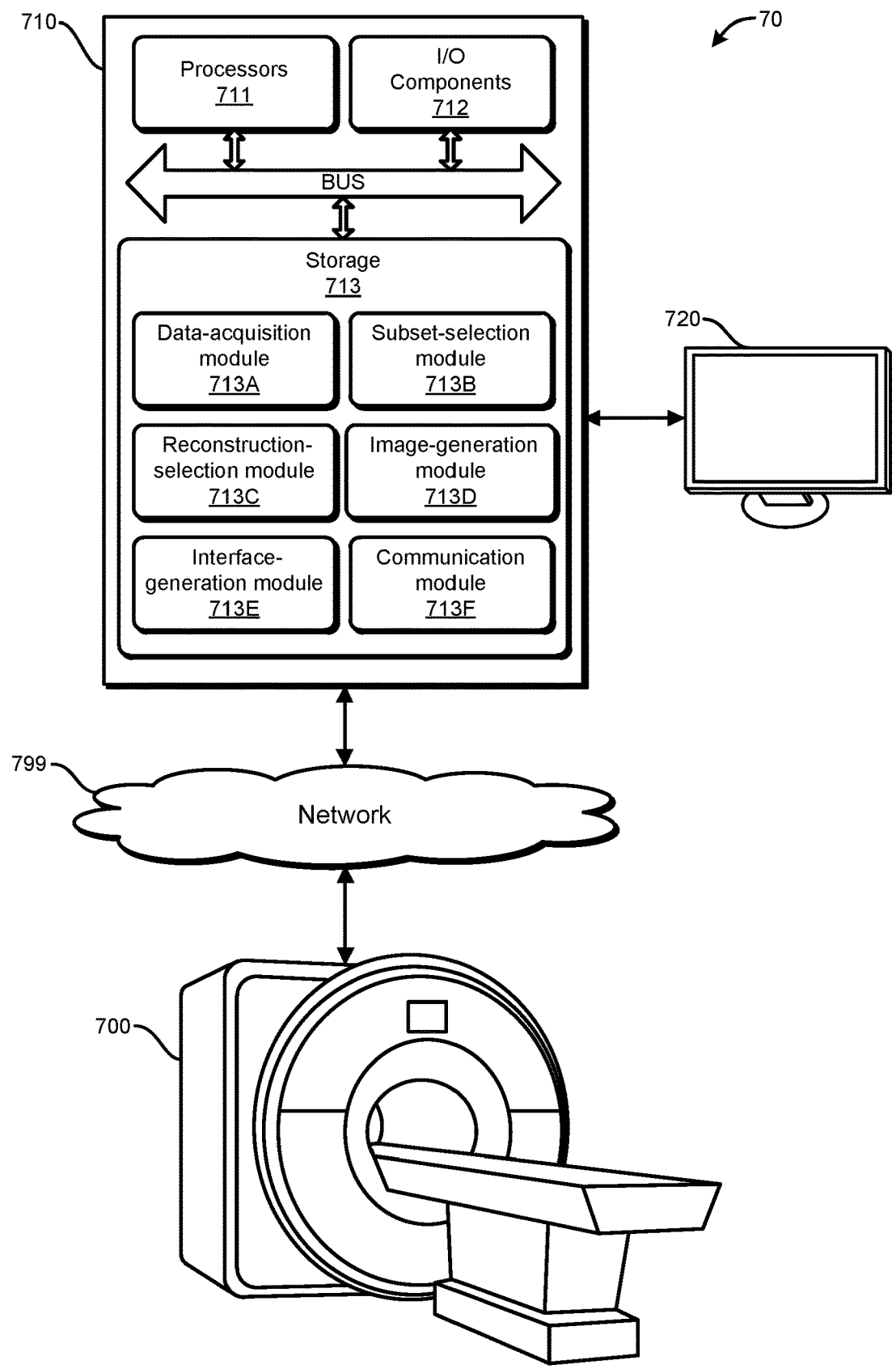
FIG. 7 illustrates an example embodiment of a medical-imaging system.

FIG. 7 illustrates an example embodiment of a medical-imaging system. The system 70 includes a scanning device 700; an image-generation device 710, which is a specially-configured computing device; and a display device 720. In this embodiment, the image-generation device 710 and the scanning device 700 communicate via one or more networks 799, which may include a wired network, a wireless network, a LAN, a WAN, a MAN, and a PAN. Also, in some embodiments the devices communicate via other wired or wireless channels.

The image-generation device 710 includes one or more processors 711, one or more I/O components 712, and storage 713. Also, the hardware components of the image-generation device 710 communicate via one or more buses or other electrical connections. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 711 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 712 include communication components (e.g., a GPU, a network-interface controller) that communicate with the display device 720, the network 799, the scanning device 700, and other input or output devices (not illustrated), which may include a keyboard, a mouse, a printing device, a touch screen, a light pen, an optical-storage device, a scanner, a microphone, a drive, and a controller (e.g., a joystick, a control pad).

The storage 713 includes one or more computer-readable storage media. As used herein, a computer-readable storage medium, in contrast to a mere transitory, propagating signal per se, refers to a computer-readable media that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 713, which may include both ROM and RAM, can store computer-readable data or computer-executable instructions.

The image-generation device 710 also includes a data-acquisition module 713A, a subset-selection module 713B, a reconstruction-selection module 713C, an image-generation module 713D, an interface-generation module 713E, and a communication module 713F. A module includes logic, computer-readable data, or computer-executable instructions. In the embodiment shown in FIG. 7, the modules are implemented in software (e.g., Assembly, C, C++, C #, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 713. Also, in some embodiments, the image-generation device 710 includes additional or fewer modules, the modules are combined into fewer modules, or the modules are divided into more modules.

The data-acquisition module 713A includes instructions that cause the image-generation device 710 to obtain scan data from the scanning device 700, for example as described in block B200 in FIG. 2; in blocks B310, B320, and B350 in FIG. 3; or in block B540 in FIG. 5.

The subset-selection module 713B includes instructions that cause the image-generation device 710 to define a subset of scan data that are defined in an acquisition space, to select (or otherwise delimit) a subset of obtained scan data, or to extract a subset of scan data from obtained scan data, for example as described in block B210 in FIG. 2, in block B300 in FIG. 3, or in block B550 in FIG. 5. Some embodiments of the subset-selection module 713B obtain an input from a user or call the interface-generation module 713E.

The reconstruction-selection module 713C includes instructions that cause the image-generation device 710 to select a reconstruction process for use on a subset of scan data and select a reconstruction process for use on a set of scan data, for example as described in blocks B500-B530 in FIG. 5. Some embodiments of the reconstruction-selection module 713C call the interface-generation module 713E.

The image-generation module 713D includes instructions that cause the image-generation device 710 to generate an image based on a subset of scan data, to generate an image based on a set of scan data, store generated images, send generated images to display devices, or send generated images to storage devices, for example as described in blocks B220-B230 in FIG. 2; in blocks B330, B340, B360, and B370 in FIG. 3, or in blocks B560-595 in FIG. 5.

The interface-generation module 713E includes instructions that cause the image-generation device 710 to generate a user interface (e.g., as shown in FIG. 6) and receive inputs from the user interface. The interface-generation module 713E may be called by other modules, for example the subset-selection module 713B or the reconstruction-selection module 713C.

The communication module 713F includes instructions that cause the image-generation device 710 to communicate with one or more other devices, for example the scanning device 700 and the display device 720.

Therefore, the image-generation device 710 can quickly generate lower-resolution images that help an operator of the scanning device 700 scan more patients and decrease or eliminate some delays in the operator's workflow. Furthermore, the image-generation device 710 also generates higher-resolution images that a physician can use to diagnose a disease or an injury. Thus, the image-generation device 710 improves an operator's utilization of the scanning device 700 while also providing higher-resolution images.

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or."

The invention claimed is:

1. A method for generating medical images, the method comprising:
   receiving scan data, wherein the scan data is defined in an acquisition space;
   performing a first reconstruction process to generate a lower-resolution image based on the scan data, wherein the first reconstruction process uses a subset of the scan data;
   performing a second reconstruction process to generate a higher-resolution image based on the scan data, wherein the second reconstruction process uses more of the scan data than the subset of the scan data, and
   displaying the lower-resolution image before the higher-resolution image is complete.

2. The method of claim 1, wherein the scan data is magnetic-resonance-imaging data.

3. The method of claim 1, further comprising: displaying the lower-resolution image as a thumbnail image.

4. The method of claim 3, further comprising: setting a scan range of a medical-imaging device based on the thumbnail image.

5. The method of claim 3, further comprising:
   sending the thumbnail image to a display device of a console of an operator of a medical-imaging device; and
   sending the higher-resolution image to a medical-image server.

6. The method of claim 1, wherein the second reconstruction process uses all of the scan data.

7. The method of claim 1, wherein the acquisition space is k-space.

8. The method of claim 7, wherein the subset of the scan data is a central part of the k-space.

9. The method of claim 1, wherein the lower-resolution image is defined in a two-dimensional image space.

10. The method of claim 1, wherein the lower-resolution image is defined in a three-dimensional image space.

11. The method of claim 1, wherein the first reconstruction process is different from the second reconstruction process.

12. The method of claim 11, wherein the first reconstruction process is faster than the second reconstruction process.

13. The method of claim 1, wherein the scan data includes data used by a compressed-sensing process.

14. A medical device comprising:
    one or more processors; and
    one or more computer-readable media that are in communication with the one or more processors and that include instructions for:
      obtaining scan data, wherein the scan data is defined in an acquisition space;
      generating a lower-resolution image based on a subset of the scan data;
      generating a higher-resolution image based on more of the scan data than the subset of the scan data; and
      displaying the lower-resolution image before the higher-resolution image is complete.

15. The device of claim 14, wherein the scan data was produced by magnetic resonance imaging, and wherein the acquisition space is k-space.

16. The device of claim 15, wherein the subset of the scan data is generated by undersampling the scan data.

17. The device of claim 14, wherein the higher-resolution image is generated based on all of the scan data.

18. The device of claim 14, wherein the generating of the lower-resolution image is started after the subset of the scan data has been received and before all of the scan data has been received.

19. The device of claim 14, wherein the one or more computer-readable media further include instructions for displaying the lower-resolution image before completing the generation of the higher-resolution image.

20. One or more computer-readable storage media storing instructions that, when executed by one or more computing devices, cause the one or more computing devices to perform operations comprising:
    obtaining scan data that is defined in an acquisition space;
    performing a first reconstruction process on a subset of the scan data, thereby generating a lower-resolution image of the scan data in an image space;
    performing a second reconstruction process on the scan data, thereby generating a higher-resolution image of the scan data in the image space; and
    displaying the lower-resolution image before the higher-resolution image is complete.

21. The one or more computer-readable storage media of claim 20, wherein the operations further comprise:
    sending the lower-resolution image to a display device before finishing the second reconstruction process.

22. The one or more computer-readable storage media of claim 20, wherein the first reconstruction process is faster than the second reconstruction process.

23. The one or more computer-readable storage media of claim 20, wherein the second reconstruction process uses some outputs of the first reconstruction process.

24. The device of claim 14, wherein a first reconstruction process generating the lower-resolution image is faster than a second reconstruction process generating the higher-resolution image.

* * * * *